(12) United States Patent
Stichelbaut

(10) Patent No.: US 6,940,944 B2
(45) Date of Patent: Sep. 6, 2005

(54) METHOD AND APPARATUS FOR X-RAY IRRADIATION HAVING IMPROVED THROUGHPUT AND DOSE UNIFORMITY RATIO

(75) Inventor: Frederic Stichelbaut, Mazy (BE)

(73) Assignee: Ion Beam Applications S. A., Louvain-La-Neuve (BE)

( * ) Notice: Subject to any disclaimer, the term of this patent is extended or adjusted under 35 U.S.C. 154(b) by 0 days.

(21) Appl. No.: 10/658,492

(22) Filed: Sep. 8, 2003

(65) Prior Publication Data

US 2005/0053194 A1 Mar. 10, 2005

(51) Int. Cl.$^7$ ............................. G21K 5/08; G21K 5/10
(52) U.S. Cl. ......................................... 378/68; 378/69
(58) Field of Search ............................. 378/64, 66, 68, 378/69

(56) References Cited

U.S. PATENT DOCUMENTS

| | | | |
|---|---|---|---|
| 4,788,701 A | * 11/1988 | Barrett | 378/69 |
| 5,396,074 A | * 3/1995 | Peck et al. | 250/453.11 |
| 6,504,898 B1 | 1/2003 | Kotler et al. | |

FOREIGN PATENT DOCUMENTS

WO    WO 03/028771    4/2003

\* cited by examiner

Primary Examiner—Craig E. Church
Assistant Examiner—Thomas R. Artman
(74) Attorney, Agent, or Firm—Merchant & Gould P.C.

(57) ABSTRACT

The present invention is related to a method and apparatus of radiation processing of a product package in a device having a radiation source, a collimator having a variable aperture, and a turntable, said radiation processing resulting in a point in the product package where the dose is minimal ($D_{min}$ point) and a point in said product package where the dose is maximal ($D_{max}$ point) comprising the steps of:

determining a first value of the collimator aperture, by increasing said aperture from a small value, where the $D_{max}$ point is located near the centre of the product package, up to a value where the $D_{max}$ point moves near to the centre of a small side of said package's rectangular horizontal cross-section;

determining a second value of the collimator aperture, by further increasing the collimator aperture up to a point where the $D_{min}$ point moves from a point near the corner of the product package to the centre of said package;

processing said package with radiation, the collimator aperture being kept at a constant value comprised between said first and said second value, the turntable being rotated at a variable speed.

7 Claims, 6 Drawing Sheets

METHOD AND APPARATUS FOR X-RAY IRRADIATION HAVING IMPROVED THROUGHPUT AND DOSE UNIFORMITY RATIO

FIELD OF THE INVENTION

The present invention is related to a method and apparatus for X-ray irradiation wherein an improved throughput and dose uniformity ratio in irradiated products can be obtained.

STATE OF THE ART

Irradiation is used to treat many types of products and articles, e.g. for sterilising medical devices, or for pasteurising food. Irradiation is also used for polymerisation of liquid monomers or degradation or cross-linking of polymers.

Depending on the level of dose required for achieving an effect, the type of irradiation source available, and the size of the products or articles, one uses gamma rays, electron beams or X-rays. These radiation types have very different properties as to penetration in matter, and the production methods are also very different (see "Radiation Sterilization for Health Care Products", B. P. Fairand, CRC Press, 2002).

An irradiation process is often specified by a minimum absorbed dose to achieve the desired effect and a maximum dose limit that the product can tolerate while still being functional (see ISO/ASTM 51649 and ISO/ASTM 51702). The dose distribution within a product is characterized by the Dose Uniformity Ratio (DUR), defined as the ratio of the maximal to the minimal dose absorbed in the product, and depends on process load characteristics, irradiation conditions and operating parameters.

Due to the non-uniformity of dose in the product (high DUR), a given product may not be treatable at a given facility because the maximum acceptable dose would be exceeded at some place while the lowest dose in the product is at the lower limit.

Electron beam may be used, but because of the limited penetration depth in matter of electrons (a few cm, in unit density material), these are not adapted for the treatment of large volumes such as whole pallets. A better solution is the use of photons, being either gamma rays or X-rays. Traditionally, the radiation source was a radioactive element producing gamma rays, such as Cobalt 60. For reasons of safety, i.a. in the disposal of waste, these systems are now replaced by systems relying on the use of an electron accelerator for producing a high-energy electron beam. This high-energy electron beam then passes through a foil made of a high-Z metal, for producing X-rays.

There is a clear industrial interest in irradiation devices where whole pallets can be treated, i.e. without depalletisation and re-palletisation of individual packages. Typically the product pallets are carrier-trays of 80×100, 80×120 or 100×120 cm², (depth×width) on which products may be stacked up to 200 cm.

X-ray pallet irradiation devices may rely on conveyor systems where product pallets are moved in a linear movement in front of an X-ray beam source. Document WO 03/028771 discloses such a device, comprising means for turning the pallet after irradtion, in order to irradiate successively two or more sides of the product pallet, for improving DUR.

Another family of irradiation systems, i.e. rotation systems, uses means for rotating a product before the radiation source. The irradiator of document U.S. Pat. No. 6,504,898 can be used for such type of irradiation. More particularly, this document is describing an apparatus and process for irradiating a product pallet using a radiation source, an adjustable collimator, a turntable on which the product pallet is loaded, a control system as well as a detection system. The process comprises the steps of (i) determining with the detection system the depth, width, height of the product pallet, as well as the density of the products on said pallet; (ii) determining the width for a collimated radiation beam required to produce a DUR of from about 1 to about 2; (iii) adjusting at least one of the following parameters in phase with turntable rotation:

collimator aperture, distance between turntable and collimator, turntable offset as a function of angular orientation of the turntable. The values of the parameters to be selected depend on product density and size.

This solution gives good DUR ratios, especially for larger density products, however at the cost of a lower throughput, because an important part of the power is lost in the collimators. Moreover, this system is expensive, because complex control and mechanical handling means are needed for the rotation table and the collimators, which need to be moved along with turntable rotation.

Another drawback of a rotating system is the multiplicity of parameters influencing dose deposition profile. It is therefore more difficult to select operating conditions and to predict DUR for the many product/apparatus parameters combinations.

AIMS OF THE INVENTION

The present invention aims to provide an irradiation method and apparatus having optimal characteristics for achieving a high throughput while the DUR is maintained below an acceptable limit.

SUMMARY OF THE INVENTION

The present invention is related to a method of radiation processing of product packages in a device having a radiation source, a collimator having a variable aperture, and a turntable, said radiation processing resulting in a point in the product package where the dose is minimal ($D_{min}$ point) and a point in said product package where the dose is maximal ($D_{max}$ point) comprising the steps of:

determining a first value of the collimator aperture, by increasing said aperture from a small value, where the $D_{max}$ point is located near the centre of the product package, up to a value where the $D_{max}$ point is located near to the centre of a small side of said package's rectangular horizontal cross-section;

determining a second value of the collimator aperture, by further increasing the collimator aperture up to a point where the $D_{min}$ point moves from a point near the corner of the product package to the centre of said package;

processing said package with radiation, the collimator aperture being kept at a constant value comprised between said first and said second value, the turntable being rotated at a variable speed.

By selecting the collimator aperture in said range, the DUR obtained is minimal.

Preferably, the collimator aperture is selected as being said second value. The throughput of the installation is thereby maximised The invention is also related to apparatus for radiation processing of packages comprising a radiation source, a collimator having a variable aperture, and a turntable, characterized in that said collimator is adapted for adjusting its aperture prior to irradiation of a package. This apparatus is less expensive to build, and less complex to maintain than the know devices.

Preferably, the ratio of collimator aperture over the distance d1 from radiation source to front face of collimator is adjustable between 0.54 and 0.73, and the ratio of collimator aperture over the distance d2 from radiation source to centre of turntable is adjustable between 0.11 and 0.16.

Furthermore, the present invention is related to the use of a method or process mentioned here above for irradiating product packages having a mean density comprised between 0.4 and 0.8 g/cm3.

SHORT DESCRIPTION OF THE DRAWINGS

Figure 4:
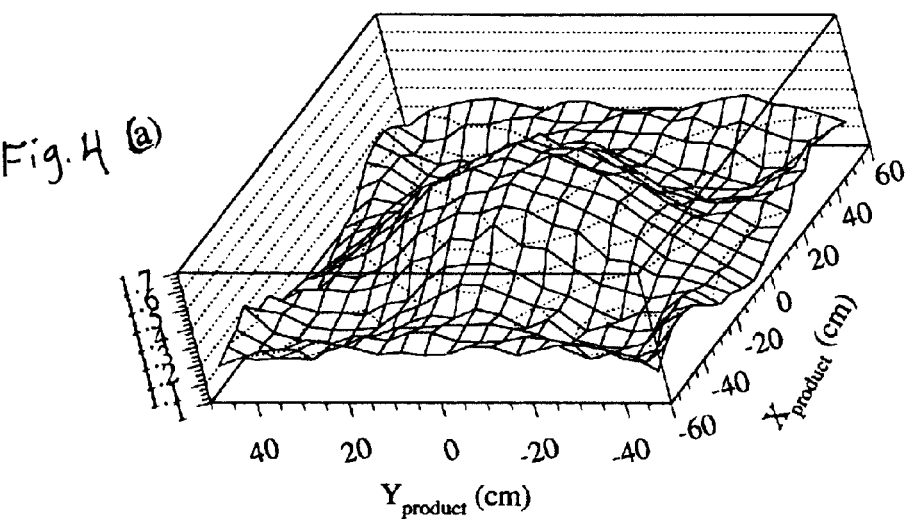
Figure 4:
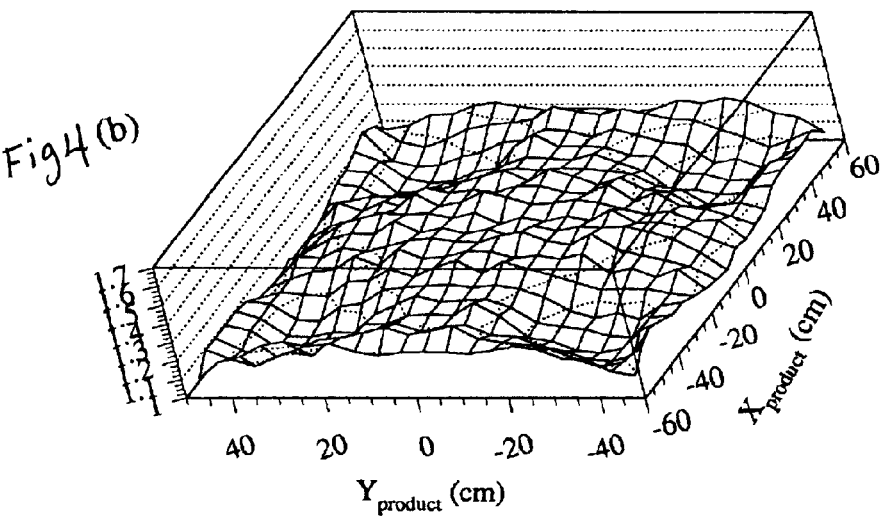
Figure 4:
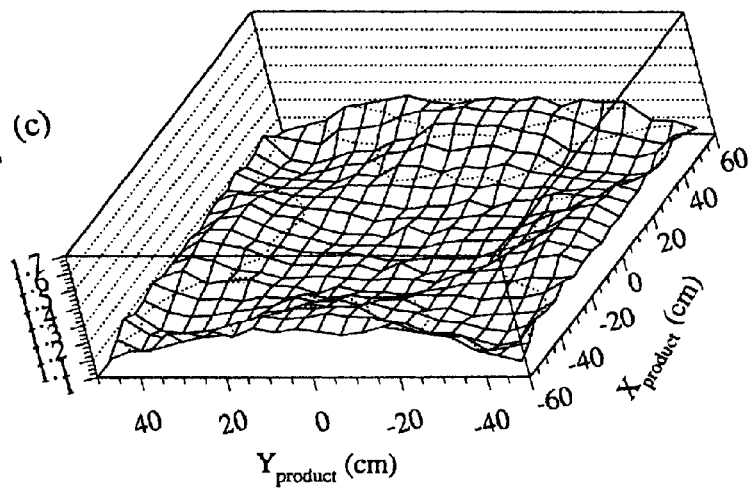
Figure 4:
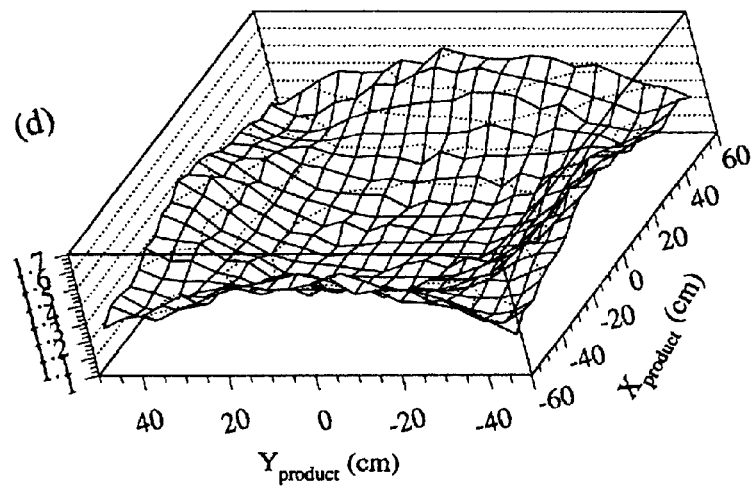

FIGS. 4a, b, c, d represent the dose distribution in a horizontal cut in a product package, for a collimator aperture of 9 cm, 12 cm, 16 cm and 20 cm, respectively; The Y-axis is graduated with respect to the minimal dose taken as unity.

Figure 5A:
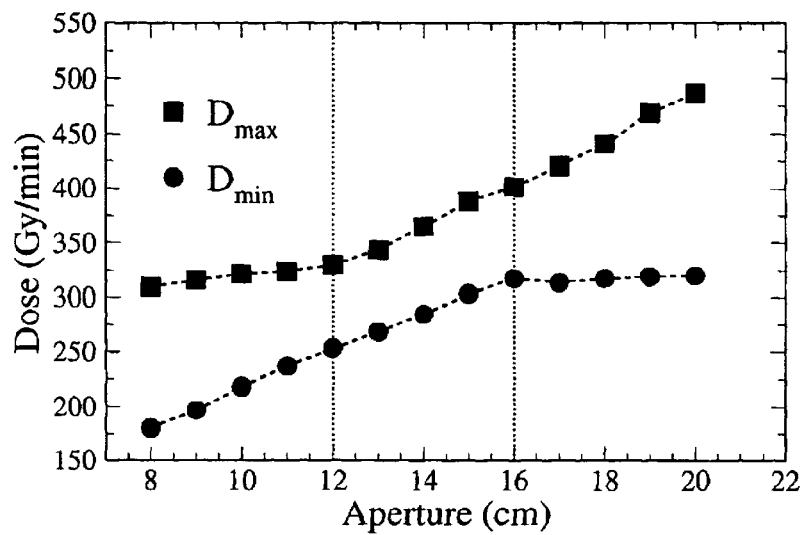
Figure 5B:
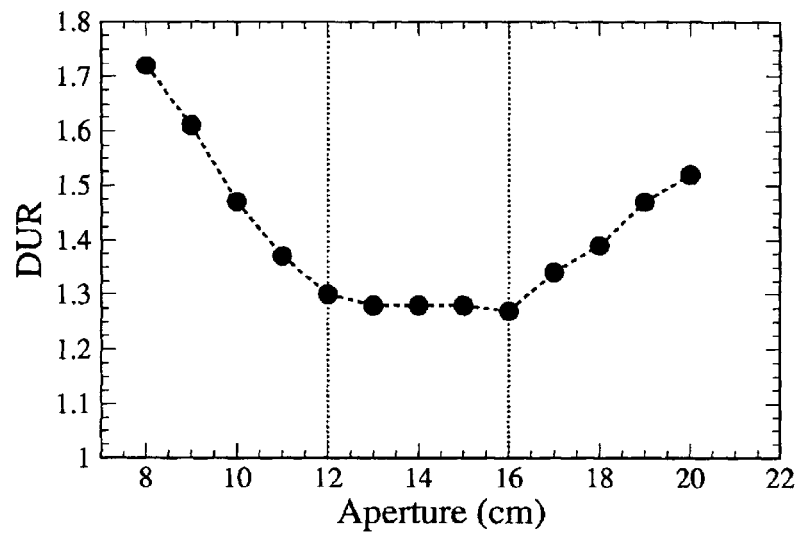

FIG. 5a represents maximum and minimum dose in a product package, as a function of collimator aperture;

FIG. 5b represents dose uniformity ratio, as a function of collimator aperture.

DESCRIPTION OF PREFERRED EMBODIMENTS OF THE INVENTION

Figure 1:
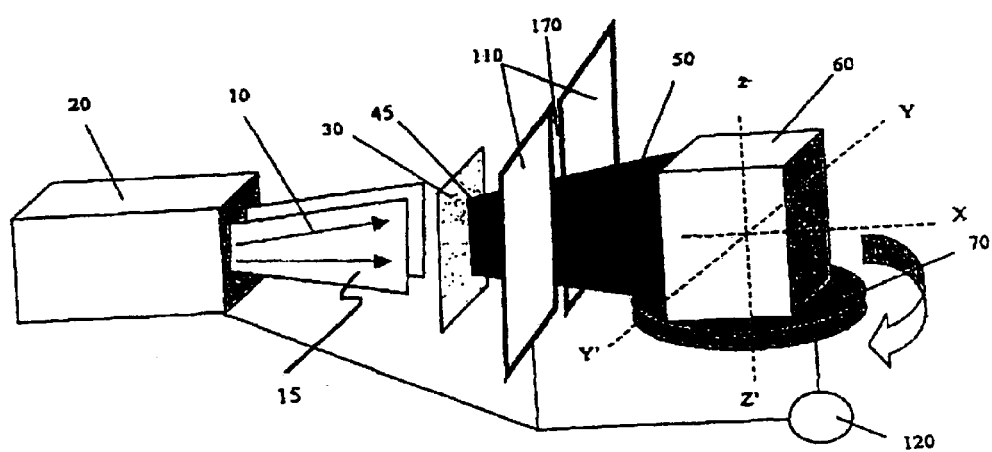
FIG. 1 represents a side perspective view of an irradiation device known in the art.

FIG. 1 is a side perspective view of an irradiation device known in the art from above-cited U.S. Pat. No. 6,504,898. An electron accelerator 20 generates an electron beam 15. Said electron beam impinges on a converter foil 30 made of a high-Z metal, for producing an X-ray beam 45. An adjustable collimator 110, made of two slabs of steel, provides an aperture 170 of variable width, for producing a collimated X-ray beam 50. A product package 60 to be irradiated is positioned centrally on a turntable 70. A control system 120 is provided for controlling the rotation speed and angle of the turntable 70, the aperture of the collimators 110, and the power of the electron accelerator 20.

Figure 2:
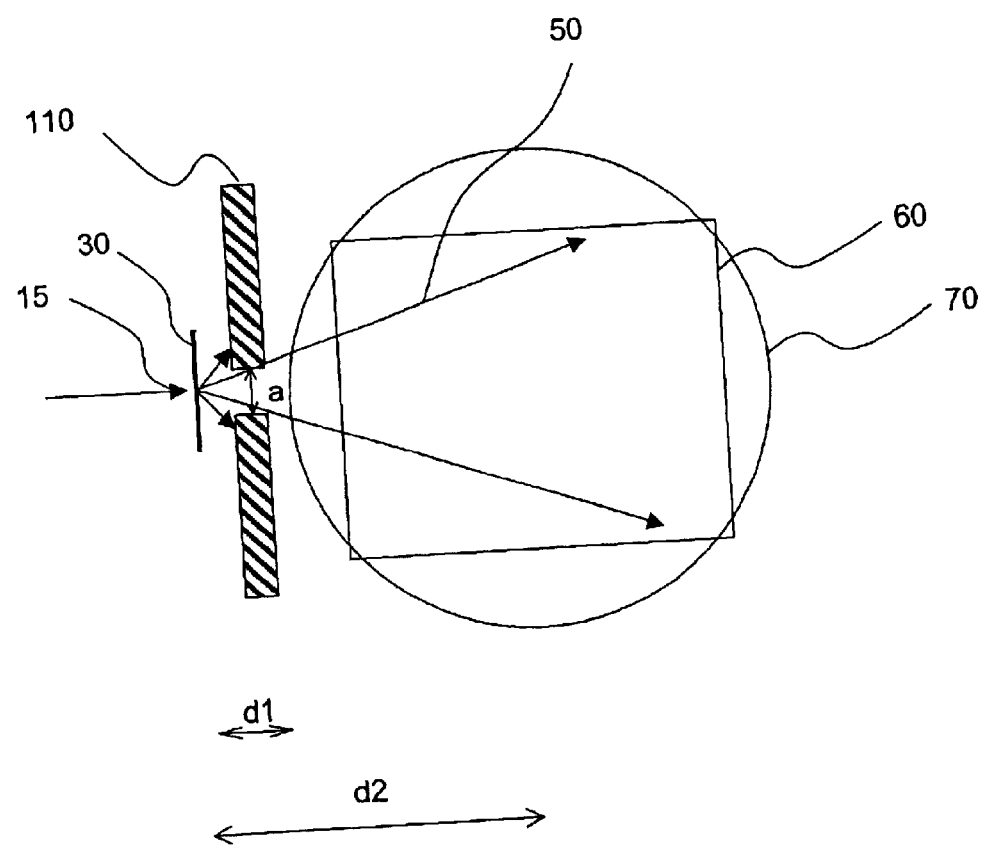
FIG. 2 represents a top view of same device.

FIG. 2 is a top view of the irradiation device of FIG. 1, where same elements have same numbers. Parameters of the irradiation process are shown: the aperture of the collimators is shown as a, the distance between front face of converter 30 and front of collimator is shown as d1, and the distance between front face of converter 30 and centre of turntable 70 and package 60 is shown as d2.

The dose deposited in the volume of the product package after irradiation in this device is determined experimentally, by using Cellulose Triacetate (CTA) dosimeter grids and radiochromic dosimeters located at various points inside the package. The dose distribution is also determined by a model simulation using the GEANT3 software package of CERN. FIG. 4a to d show the results obtained from a GEANT3 simulation with a 100 cm×120 cm pallet loaded with a product having a density of 0.8 g/cm3. An electron beam having energy of 7 MeV impinges on a converter comprising successively a Tantalum foil having a thickness of 1.2 mm, a layer of cooling water having a thickness of 2 mm, and a 2 mm stainless steel sheet. Geometrical parameters were as follows: distance d1 between converter foil and front side of collimators d1: 22 cm; thickness of collimator: 10 cm; distance d2 between converter foil and centre of product package: 103 cm.

Figure 3:
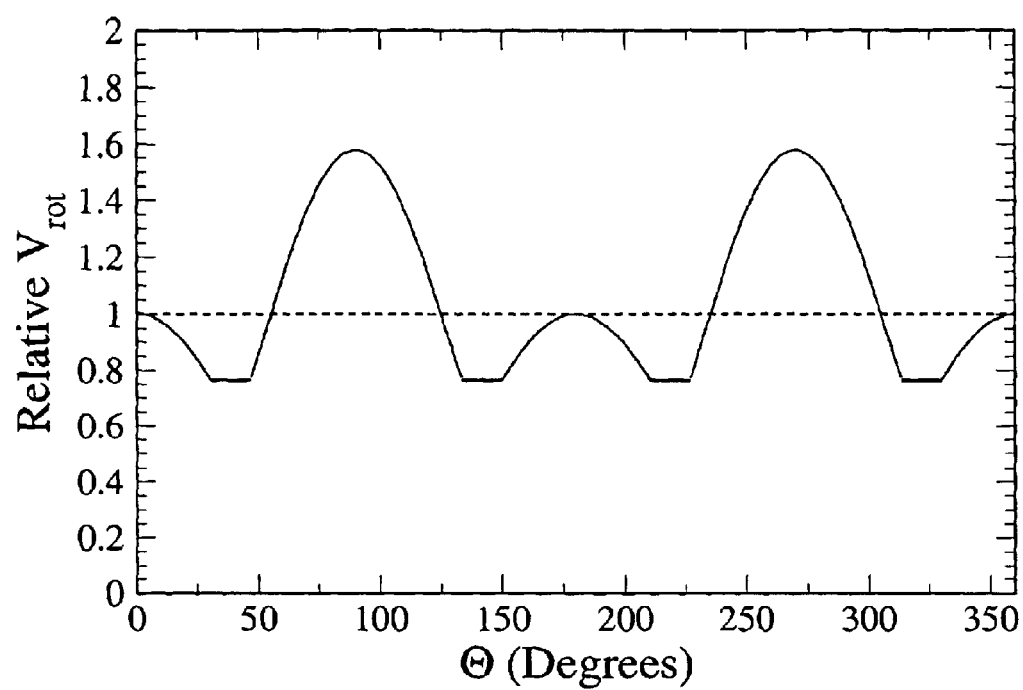
FIG. 3 represents rotational speed profile as a function of angular orientation of the turntable.

FIG. 3 represents rotational speed profile as a function of angular orientation of the turntable. Starting at a unit speed from the 0° orientation where the small face of the product package is oriented towards the radiation source, the rotational speed is reduced, for irradiating the corners at a reduced relative speed of 0.75, and then increased again for irradiating the large face of the product package, at 90°, at an increased relative speed of 1.6. In above-cited U.S. Pat. No. 6,504,898, this effect is obtained by varying the beam intensity inversely, giving more intensity near the corners, and less at the faces. Both techniques produce equivalent dose distributions. However, the variation of angular rotation speed allows using the electron accelerator 20 permanently at its rated power, and therefore provides a more efficient method.

In examining the dose distribution in a horizontal plane of a rectangular product package, at mid-height, or at about mid-height, one observes the following situation. Rotational speed is varied as shown on FIG. 3, and the collimator aperture is kept constant during irradiation. Various increasing values of the aperture are considered. The points in the package where the dose is maximum and minimum are called the $D_{max}$ and the $D_{min}$ point, respectively. When using a small collimator aperture (e.g. 9 cm, as shown in FIG. 4a), the dose is maximum in the central area of the package. This results from the fact that this area is permanently in the direction of the narrow beam. When increasing the collimator aperture, the dose in the centre increases slightly, because some photons, not directed towards the centre, are scattered towards the centre by surrounding material. The point with the minimal dose is located on the face of the large side of the package. This $D_{min}$ value will increase more sharply when increasing the collimator aperture, because it will receive more and more direct photons from the side wings of the beam.

When going on with increasing the collimator aperture, at some point the $D_{max}$ point will move to the centre of a small side of the package and the $D_{min}$ point will be located near a corner. This is the situation shown on FIG. 4b for a collimator aperture of 12 cm.

When still increasing the collimator aperture, at some point the $D_{min}$ point will move to the centre of the package and the $D_{max}$ point will remain at the centre of a small side. This is the situation shown on FIG. 4c for a collimator aperture of 16 cm.

Beyond that aperture value, the $D_{min}$ point remains in the centre, and the dose does not increase anymore, for the above stated reason. The $D_{max}$ value still increases with collimator aperture. This is the situation shown of FIG. 4d for a collimator aperture of 20 cm.

The resulting DUR, being the ratio of $D_{max}$ over $D_{min}$, is shown on FIG. 5b. This clearly shows 3 distinct regions: a first region for apertures between 8 and 12 cm, where DUR decreases; a second region for apertures between 12 and 16 cm where DUR remains essentially constant, at about 1.3; and a third region, for apertures above 16 cm, where DUR increases again.

The method of the invention is about the use of a fixed collimator aperture in the second region. The method comprises the step of first determining this region, by increasing the collimator aperture, from a small value where the $D_{max}$ point lies in the centre of the package, up to a first value for which the $D_{max}$ point moves to the centre of a small side of the package's rectangular horizontal cross-section. This step is followed further increasing the aperture for the determination of a second value for which the $D_{min}$ point lies in the centre of the package. The second region mentioned above is determined by this first and second value. This second region may be located for different values of the actual collimator aperture, depending on the other parameters of the process. Other determinant parameters include package size, product density, distance from source to collimator, distance from source to package, collimator thickness. The aperture limits of 12 and 16 cm apply for the above cited parameter values. This corresponds to a ratio of the aperture over the distance d1 between 0.54 and 0.73, and of aperture over the distance d2 between source and centre of turntable between 0.11 and 0.16.

The invention is especially useful for products having higher densities, i.e. above 0.4 g/cm3, where obtaining low DUR and high throughput is difficult. The best throughput for an installation with an electron accelerator having a given power is obtained when the $D_{min}$ value is the highest, or when a given $D_{min}$ is obtained in the shortest time. This is obtained by selecting the aperture at the upper limit of the second zone, i.e. 16 cm, in the present example.

It will be apparent from the foregoing that, while particular forms of the invention have been illustrated and described, various modifications can be made without departing from the spirit and scope of the invention. Moreover, those skilled in the art will recognize that features shown in one embodiment may be utilized in another embodiment. In other instances, well-known equipment or process operations may be found missing in the embodiment descriptions. Those well known features have not been described in detail in order not to unnecessarily obscure the present invention.

The invention is not to be construed as limited to the above detailed description. More specifically, although the above description shows variation of the rotation speed, the invention would equally apply to variation of beam intensity, in an inverse way.

What is claimed is:

1. A method of radiation processing of a product package o of essentially equal rectangular size in a device having a radiation source, a collimator having a variable aperture, and a turntable, said radiation processing resulting in a point in the product package where the dose is minimal ($D_{min}$ point) and a point in said product package where the dose is maximal ($D_{max}$ point) comprising the stops of:

determining a first value of the collimator aperture, by increasing said aperture from a small value, where the $D_{max}$ point is located near the centre of the product package, up to a value where the $D_{max}$ point moves near to the centre of a small side of said package's rectangular horizontal cross-section;

determining a second value of the collimator aperture, by further increasing the collimator aperture up to a point where the $D_{min}$ point moves from a point near the corner of the product package to the centre of said package;

processing said package with radiation, the collimator aperture being kept at a constant value comprised between said first and said second value, the turntable being rotated at a variable speed.

2. The method according to claim 1, wherein the collimator aperture is selected as being said second value.

3. The method according to claim 1, wherein said product package has a mean density between 0.4 and 0.8 g/cm$^3$.

4. Apparatus for radiation processing of package of essentially equal rectangular size, comprising a radiation source, a collimator having a variable aperture, and a turntable, adapted for supporting one of said packages during said radiation processing, wherein said apparatus comprises a means for:

determining a first value of the collimator aperture, by increasing said aperture from a small value, where a $D_{max}$ point is located near tho centre of the product package, up to a value where the $D_{max}$ point moves near to the centre of a small side of said package's rectangular horizontal cross-section; and determining a second value of the collimator aperture, by further increasing the collimator aperture up to a point where a $D_{min}$ point moves from a point near the corner of the product package to the centre of said package; and wherein said collimator is adapted far adjusting its aperture to a value comprised between said first and second value, prior to irradiation of the package.

5. The apparatus according to claim 4, wherein the ratio of collimator aperture over a distance d1 from radiation so to front face of collimator is adjustable between 0.54 and 0.73.

6. The apparatus according to claim 4, wherein the ratio of collimator aperture over a distance d2 from radiation source to centre of turntable is adjustable between 0.11 and 0.16.

7. The apparatus according to claim 4, wherein product packages having a mean density between 0.4 and 0.8 g/cm$^3$ are irradiated.

* * * * *